United States Patent [19]

Gude et al.

[11] Patent Number: 4,571,426
[45] Date of Patent: Feb. 18, 1986

[54] PROCESS FOR THE PRODUCTION OF MALEIC ANHYDRIDE

[75] Inventors: Fritz Gude, Herne; Ferdinand von Praün, Haltern, both of Fed. Rep. of Germany

[73] Assignee: Chemische Werke Huls AG, Marl, Fed. Rep. of Germany

[21] Appl. No.: 646,155

[22] Filed: Aug. 31, 1984

[51] Int. Cl.⁴ .......................................... C07D 307/60
[52] U.S. Cl. .................................. 549/257; 549/258; 549/259; 549/260; 549/262
[58] Field of Search .............. 549/257, 258, 259, 260, 549/262

[56] References Cited

U.S. PATENT DOCUMENTS 3,833,619 9/1974 Baumann et al. ................... 549/261
3,931,243 1/1976 Paustian et al. ..................... 549/247

*Primary Examiner*—Richard L. Raymond
*Attorney, Agent, or Firm*—Oblon, Fisher, Spivak, McClelland & Maier

[57] ABSTRACT

A process for the production of maleic anhydride by catalytic air oxidation of hydrocarbons capable of being so oxidized at a temperature in the range of 300°–450° C., which, after air oxidation, entails:

(a) introducing the air stream containing maleic anhydride and water vapor
  (i) at a temperature below the dew point of the accompanying water, into a water-insoluble tertiary amine extracting agent, which is stable to air, and a hydrocarbon diluent entrainer for the water; and separating the formed organic layer; or
  (ii) at a temperature above the dew point of the accompanying water, into a mixture of a water-insoluble tertiary amine extracting agent, which is stable to air, and a high-boiling alcohol; and separating the formed organic layer; or
  (iii) into water; and extracting the maleic acid with a water-insoluble tertiary amine extracting agent, which is stable or unstable to air, and a hydrocarbon diluent entrainer for the water; and separating the formed organic layer; and
(b) heating the extract obtained according to step (a) to a temperature in the range of 120°–180° C. in vacuo, thereby recovering the maleic anhydride; and wherein said water-insoluble tertiary amines have a pKa value <9, and wherein said tertiary amines, for steps (a) (i) and (a) (ii) have branched primary aliphatic side chains in the 2-position.

10 Claims, 1 Drawing Figure

PROCESS FOR THE PRODUCTION OF MALEIC ANHYDRIDE

BACKGROUND OF THE INVENTION

1. Field of the Invention

The present invention relates to a process for the production of maleic anhydride by catalytic air oxidation of suitable hydrocarbons.

2. Description of the Prior Art

In the air oxidation of hydrocarbons, such as benzene, butane, butene or butadiene to maleic anhydride and water at about 400° C., mainly even-numbered lower carboxylic acids, carbon monoxide and carbon dioxide are formed as by-products. In order to recover as much maleic anhydride as possible directly in solid form from the oxidation stream, the air stream with the resulting substances is cooled, inter alia, to temperatures above the dew point of the accompanying water to prevent hydrolysis. In this way, it is possible to separate up to about 85% by weight of the resulting maleic anhydride immediately after benzene oxidation and up to about 30–50% by weight immediately after butane/butene oxidation. To recover the remaining amount, the gas stream containing the maleic anhydride is scrubbed with so much water that the anhydride is virtually completely precipitated. Thereby an approximately 40% maleic acid solution is formed by hydrolysis. In order to, again, recover maleic anhydride therefrom, according to the conventional wisdom in the art, inter alia, all the water is distilled off from the top of a suitable column by an expensive, energy-consuming process with the addition of entrainer, e.g., xylene, whereby the maleic anhydride is re-formed from the maleic acid. In addition, a small amount of fumaric acid is also formed by cis-trans-isomerization.

Of course, it is also possible to dispense entirely with the separation of the solid maleic anhydride by the corresponding cooling of the oxidation stream and instead of this, to scrub the total oxidation gas immediately after it leaves the reactor. This can be advantageous above all after oxidation of $C_4$ gases, since because of the higher dew point of the water only a relatively small amount of maleic anhydride can be recovered directly by cooling of the oxidation stream. Unfortunately, this manner of operation is particularly costly in energy.

For this reason, many proposals have suggested the avoidance of the gas stream scrubbing with water. Thus in U.S. Pat. No. 3,198,680 it is recommended that the esters of phthalic acid with $C_4$–$C_6$ alcohols be used as the scrubbing medium. EP-AS No. 00 19 046 uses cycloaliphatic acid esters as the scribbing medium. In DE-OS No. 2 444 824 dibenzylbenzene and in EP-PS No. 1 443 411 polymethylbenzophenones are proposed as scrubbing liquids.

Besides other disadvantages, the recommended solvents above all exhibit slight extraction effects especially under the operating conditions of the process, which are caused by the fact that the large oxidation gas stream largely removes the maleic anhydride from the organic medium.

Therefore, the extraction of the maleic anhydride with inert organic media in the air oxidation process has led only to a modest success. However, the carboxylic groups resulting from hydrolysis or alcoholysis of the maleic anhydride should bind intensively to suitable basic extracting agents. To be able to separate excess water, the extracting agent must not be soluble in it. Further, the bond with the maleic acid should break by a simple process—if possible merely by heating of the extract—and, after formation of the maleic anhydride, a clean separation from the resulting water should also occur. The extracting agent must be able to be reused.

A process described by M. I. Yakushkin (SU-PS No. 168 674) relates to the isolation of lower monocarboxylic acids such as formic, acetic, propionic and butyric acid, by extraction from aqueous solutions with water-insoluble trioctylamine. The acids can be released from the resulting salt after separation of the water by heat treatment.

It was then found that maleic acid, a dicarboxylic acid, can also be extracted to some extent from aqueous solutions with tri-n-octylamine. Unfortunately, tri-n-octylamine is insufficiently stable to atmospheric oxygen and presents severe drawbacks when used as an extracting agent for maleic anhydride. Moreover, the current methods in use for producing maleic anhydride suffer from low product yields.

Therefore, a need clearly continues to exist for a process for the production of maleic anhydride which uses an extracting agent which does not suffer from insufficient stability to air and which produces maleic anhydride in excellent yield.

SUMMARY OF THE INVENTION

Accordingly, it is an object of the present invention to provide a process for the production of maleic anhydride which utilizes tertiary amines, as extracting agents, which have excellent stability to air.

It is also an object of the present invention to provide a process for the production of maleic anhydride which provides increased and excellent yields of maleic anhydride.

It is also an object of this invention to provide a process for the production of maleic anhydride which does not require disadvantageous and uneconomical amounts of energy.

According to the present invention, the foregoing and other objects are attained by providing a process for the production of maleic anhydride by catalytic air oxidation of hydrocarbons capable of being so oxidized at a temperature in the range of 300°–450° C., which, after air oxidation, entails (a) introducing the air stream containing maleic anhydride and water vapor (i) at a temperature below the dew point of the accompanying water, into a water-insoluble tertiary amine extracting agent, which is stable to air, and a hydrocarbon diluent entrainer for the water; and separating the formed organic layer; or (ii) at a temperature above the dew point of the accompanying water, into a mixture of a water-insoluble tertiary amine extracting agent, which is stable to air, and a high-boiling alcohol; and separating the formed organic layer; or (iii) into water; and extracting the maleic acid with a water-insoluble tertiary amine extracting agent, which is stable or unstable to air, and a hydrocarbon diluent entrainer for the water, and separating the formed organic layer; and (b) heating the extract obtained to a temperature in the range of 120°–180° C. in vacuo, thereby recovering the maleic anhydride, and wherein the water-insoluble tertiary amines have a pKa value <9, and wherein the tertiary amines have branched primary aliphatic side chains.

BRIEF DESCRIPTION OF THE DRAWINGS

Other objects, features and attendant advantages of the present invention will be more fully appreciated as the same becomes better understood from the following detailed description when considered in connection with the accompanying drawing and wherein.

DETAILED DESCRIPTION OF THE PREFERRED EMBODIMENTS

Figure 1:
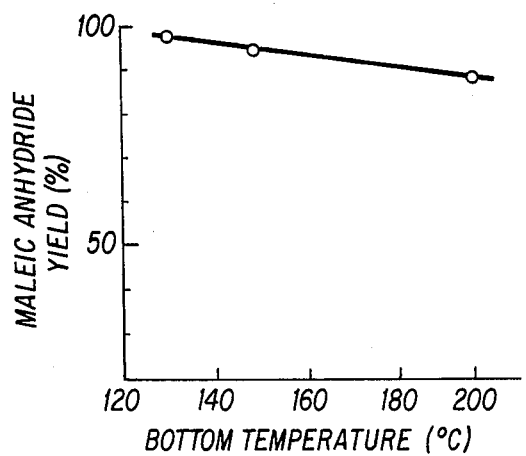
FIG. 1 illustrates the relationship between maleic anhydride yield and the bottom temperature or the still temperature in continuous distillation.

In the search for water-insoluble tertiary amines resistant to a great amount of air under operating conditions it has been now surprisingly found that certain branched carbon chains greatly increase the stability of the base. Thus, for example, tri-(2-ethylhexyl)-amine has been found to withstand bubbling through of air, even in the absence of oxidation inhibitors, for weeks practically without degradation.

One of the process methods according to the present invention is as follows: the air stream is brought from the reactor with the resulting substances, optionally after cooling to a temperature just a little above the water dew point to separate the maleic anhydride, then under the dew point of the water, optionally after addition of more water, in a liquid, water-insoluble tertiary amine that is stable to the air, e.g., tri(2-ethylhexyl)-amine. The tertiary base can be diluted with inert hydrocarbons, preferably aromatic hydrocarbons. By the precipitating water, maleic anhydride hydrolyzes to maleic acid, which is bound by the tertiary amine. The resulting oily salt is also insoluble in water. After separation of the water from the organic layer, the amine-maleic acid addition compound is then transferred to a distillation apparatus. Upon heating to about 120°–180° C. in vacuo, a splitting into amine, maleic anhydride and also water occurs; the water is separated by addition of an entrainer. The pure maleic anhydride is recovered by distillation. An apparatus, such as described in "Ullmanns Encyklopaedie der technischen Chemie," 4th edition, vol. 16, pp. 407–411, is advantageously used for this process. As was found, a phase separation occurs between maleic ahydride and amine above 50° C. after removal of the entrainer by distillation. For milder treatment, after separation, the maleic anhydride can then be purified by distillation, while the amine can be directly recycled.

In an alternative to this method of operation, after oxidation—optionally after separation of a part of the maleic anhydride by cooling to a temperature above the dew point of the accompanying water—the air-water-maleic anhydride mixture can be channeled, also above the water dew point, through a mixture of a suitable high-boiling alcohol with the tertiary amine. Thereby a semiester is formed by ring opening of the maleic anhydride, while the carboxyl group reacts with the amine to form a salt. In this way, practically the entire maleic anhydride amount is scrubbed from the air stream. By heating of this dry scrubbing liquid to about 160° C. and under a low vacuum, a splitting of the components occurs under distillation of the maleic anhydride. Thereby diesters of the alcohol used can form as by-products. Suitable alcohols are particularly those boiling above 220° C. or their mixtures such as, for example, decanol, isodecanol, lauryl alcohol, myristyl alcohol, palmityl alcohol, butyl diglycol, or mixtures thereof. Oxidation by the air is inhibited by the amine.

Finally, according to the invention, it is also possible first to stay with the usual process until before the distillation of the water after water scrubbing of the gas stream containing the maleic anhydride. The maleic anhydride hydrolizes to maleic acid by scrubbing with water. To avoid the high energy expenditure in distilling the water, the maleic acid is extracted with water-insoluble tertiary amines. In this process method, besides the branched tertiary amines already mentioned, it is also possible to use tertiary amines sensitive to oxygen, e.g., tri-n-hexylamine, tri-n-octylamine, tri-n-dodecylamine, tri-(3,5,5-trimethylhexyl)-amine, tri-(3,5,5-trimethyloctyl)-amine, tri-(3,5,5-trimethyldecyl)-amine, N,N-dioctyl-(2-ethylhexyl)-amine, N-octyl-N-(4-heptyl)-(2-ethylhexyl)-amine, N-octyl-N-(4-heptyl)-cyclohexylamine, N-octyl-N-(2-ethylhexyl)-cyclohexylamine, N-dodecyl-3,3,5-trimethylazacycloheptane, and N,N-dioctylaniline. Treatment of the resulting salt occurs as before by distillation of the maleic anhydride, after the resulting water passes over azeotropically by addition of an entrainer.

Suitable extracting agents are all water-insoluble tertiary amines with a $pK_A$ value less than 9, which are liquid under the reaction conditions, and whose salts must also be water-insoluble with maleic acid. If extraction is supposed to be direct from the reaction gases containing great amounts of air, branched tertiary amines with branched primary aliphatic side chains in the 2-position, which are stable to air under the reaction conditions, are recommended for use, e.g., tri-(2-ethylhexyl)-amine, tri-(2-ethylbutyl)-amine or tri-(2-ethyldecyl)-amine, to example. The tertiary amines remaining as still residue after distillation of the maleic anhydride could be used repeatedly for the subsequent charges without purification.

The salts from maleic anhydride and tertiary amines with branched primary aliphatic side chains in the 2-position, under a heat load, split into their components at about 30° C. less than the components of maleic acid with unbranched tertiary amines. The release of maleic acid occurring at lower temperatures is mild on the substances and particularly raises the yields of recoverable maleic anhydride to approximately quantitative values. For this reason, the use of tertiary amines with branched primary aliphatic side chains in the 2-position is preferred.

The spontaneous conversion of maleic anhydride and its semiesters and polymerization of the resulting reaction products under the catalytic action of tertiary amines described in GB-PS No. 933 102 could not be confirmed in this process under the conditions according to the present invention with said tertiary amines, as the examples below evidence. Of course, for mildness toward the substances and thereby for increasing the maleic anhydride yield and for keeping the tertiary amine clean, it is advantageous to keep the bottom temperature during distillation as low as possible. Thus, when tri-(2-ethylhexyl)-amine is used as the extracting agent, 98% of theory of the extracted maleic anhydride could be recovered by distillation at 15 mbar (bottom temperature of about 130° C.).

While the general air oxidation of hydrocarbons to maleic anhydride is known, the particular combination involved in the present invention is quite different from conventional processes with corresponding differences in end results. For example, the present process is not only an energy-saving process, but also provides for increased and excellent yields of maleic anhydride.

The object of the present invention is therefore a process for the production of maleic anhydride by catalytic air oxidation of suitable hydrocarbons, such as butene, butane, butadiene or benzene and/or their mixtures at temperatures of about 300°–450° C., wherein the following steps occur subsequent to air oxidation:

1. An optional partial separation of the maleic anhydride by cooling to temperatures above the dew point of the accompanying water.
2. Introduction of the air stream containing maleic anhydride and water vapor:
   (a) below the dew point of the accompanying water, optionally with more water being added, in a water-insoluble tertiary amine which is stable to air, which contains a hydrocarbon entrainer for the water and separation of the organic layer, or
   (b) above the dew point of the accompanying water in a mixture of water-insoluble tertiary amine, which is stable to air, and of alcohol of slight vapor pressure and separation of the organic layer, or
   (c) in water and subsequent extraction of the maleic acid with a water-insoluble tertiary amine, which contains a hydrocarbon entrainer for the reaction water and separation of the organic layer, wherein the water-insoluble tertiary amines, used as extracting agent, have a $pK_A$ value <9 and in the case of process steps 2a and 2b carry branched primary aliphatic side chains in the 2-position.
3. Heating of the extract obtained according to (2) to temperatures of 120°–180° C. in vacuo for recovery of the maleic anhydride.

The present invention will now be further illustrated by certain examples and references which are provided for purposes of illustration only and are not intended to limit the present invention.

EXAMPLES (1) 1000 g. of a 29.6% aqueous maleic acid solution was intensively subjected to solvent extraction in a single extraction step with a mixture of 1500 g of tri-(2-ethylhexyl)-amine and 1500 g of xylene. The organic extract then contained 94% of the maleic acid used. It was heated in a water separator to boiling and 105 ml of water separated at a bottom temperature of 130° C. and a pressure of 700 mbar. The residue was then subjected to vacuum distillation. After removal of the entrainer by distillation, 230.4 g of maleic anhydride distilled over at 100°–105° C./15 mbar, corresponding to a yield of 98% of theory. Small amounts of fumaric acid could still be detected in the bottom discharge which basically contained the high-boiling amine. The bottom can be reused for further maleic acid extractions without any purification.

(2–5) 1000 g of a 34.7% aqueous maleic acid solution was subjected to solvent extraction three times with a mixture of 1000 g of amine and 1000 g of diethylbenzene for 15 minutes. Between 140 and 170 ml of water was separated from the extract containing maleic acid in a water separator at a bottom temperature of 160°–165° C. and a pressure of 300 mbar. The residue was then treated by distillation and yielded boiling maleic anhydride at 100°–105° C./15 mbar.

| Amine | Extraction Rate (%) | Splitting Rate (%)+ |
|---|---|---|
| Tri-n-dodecylamine | 99.7 | 92.8 |
| Tri-n-octylamine | 99.8 | 70.0 |
| N—dodecyl-3,3,5-trimethylazacycloheptane | 98.8 | 54.8 |
| N,N—dioctylaniline | 88.0 | 59.1 |

+Splitting rate = yield in maleic anhydride.

(6) In the production of maleic anhydride by catalytic air oxidation of hydrocarbons, such as benzene, the reaction gas first is conducted through a partial condenser, in which a part of the anhydride is separated. The discharge gas leaving the separator was treated countercurrent in an extraction column with a mixture of about 50% by weight of tri-(2-ethylhexyl)-amine and 50% by weight of xylene below the dew point of the accompanying water (about 30° C.) to recover the remainder of the maleic anhydride.

3035 g of an extract recovered in this way consisting essentially of 1500 g of amine, 1395 g of xylene and 90 g of maleic acid was brought per hour to the upper half of a distillation column, which was operated at a bottom temperature of 130° C. at a pressure of 700 mbar. 54 g of water formed hourly at the top of the column in an azeotropic mixture with xylene, while the bottom product of amine, xylene and maleic anhydride was drawn off at the bottom and brought to a second column for purification by distillation. Here the remaining entrainer was distilled off at the top of the column and 75 g/h of pure maleic anhydride was isolated in the side stream of the column at a temperature of 160° C. and a pressure of 200 mbar. The maleic anhydride yield, relative to thermolysis, amounted to 98.6% of theory. The amine in the bottom after purification was recycled, with the separated xylene, to the extraction stage.

(7) The discharge gas from the maleic anhydride production (cf example 6) was treated countercurrent in an extraction column with a mixture of about 30% tri-(2-ethylhexyl)-amine, 18% lauryl alcohol and 52% dodecane at a temperature above the dew point of the accompanying water.

2950 g of the extract forming in this case, mainly 104 g of amine, 1272 g of amine salt of the maleic acid lauryl semiester, 120 g of lauryl alcohol and 1400 g of dodecane, was brought per hour to the column of a continuously operating distillation apparatus, which was operated with a bottom temperature of 160°–170° C. at a pressure of 200 mbar. A mixture of 176 g of maleic anhydride and 840 g of dodecane was formed hourly at the top of the column; the mixture separated into two liquid phases at 55°–60° C. The upper dodecane phase was recycled and the lower anhydride phase was further purified by distillation. The bottom product from the thermal decomposition, consisting of amine, dodecane and lauryl alcohol still contained lauryl maleate, which was filtered off before recycling the mixture to the extraction stage. Maleic anhydride yield in semiester thermolysis: 90% of theory.

Having now fully described this invention, it will be apparent to one of ordinary skill in the art that many changes and modifications can be made thereto without departing from the spirit or scope of the invention as set forth herein.

What is claimed as new and is intended to be secured by Letters Patent is:

1. A process for the production of maleic anhydride by catalytic air oxidation of hydrocarbons capable of being so oxidized at a temperature in the range of 300°–450° C., which, after air oxidation, comprises:
   (a) introducing the air stream containing maleic anhydride and water vapor
      (i) at a temperature below the dew point of the accompanying water, into a water-insoluble tertiary amine extracting agent, which is stable to air, and a hydrocarbon diluent entrainer for the water; and separating the formed organic layer; or
      (ii) at a temperature above the dew point of the accompanying water, into a mixture of a water-insoluble tertiary amine extracting agent, which is stable to air, and a high-boiling alcohol; and separating the formed organic layer; or
      (iii) into water; and extracting the maleic acid with a water-insoluble tertiary amine extracting agent, which is stable or unstable to air, and a hydrocarbon diluent entrainer for the water; and separating the formed organic layer; and
   (b) heating the extract obtained according to step (a) to a temperature in the range of 120°–180° C. in vacuo, thereby recovering the maleic anhydride; and wherein said water-insoluble tertiary amines have a pKa value <9, and wherein said tertiary amines, for steps (a)(i) and (a)(ii) have branched primary aliphatic side chains in the 2-position.

2. The process according to claim 1, wherein said tertiary amines have branched primary aliphatic side chains in the 2-position for steps (a)(i), (a)(ii) and (a)(iii).

3. The process according to claim 1, wherein said tertiary amines having stability to air and which are used in steps (a)(i) and (a)(ii) are tri-(2-ethylhexyl)-amine, tri-(2-ethylbutyl)-amine, tri-(2-ethyldecyl)-amine or a mixture thereof.

4. The process according to claim 1, wherein said tertiary amines which are used in step (a)(iii) are tri-(2-ethylhexyl)-amine, tri-2(ethylbutyl)-amine, tri-2(ethyldecyl)-amine or a mixture thereof, being stable to air, and tr-n-hexylamine, tri-n-octylamine, tri-n-dodecylamine, tri-(3,5,5-trimethylhexyl)-amine, tri-(3,5,5-trimethyloctyl)-amine, tri-(3,5,5-trimethyldecyl)-amine, N,N-dioctyl-(2-ethylhexyl)-amine, N-octyl-N-(4-heptyl)-(2-ethylhexyl)-amine, N-octyl-N-(4-heptyl)-cyclohexylamine, N-octyl-N-(2-ethylhexyl)-cyclohexylamine, N-dodecyl-3,5,5-trimethyl-azacycloheptane or N,N-diocylaniline or a mixture thereof, being sensitive to air.

5. The process according to claim 1, wherein said high-boiling alcohol of step (a)(ii) is an alcohol having a boiling point in excess of 220° C.

6. The process according to claim 5, wherein said high-boiling alcohol is selected from the group consisting of decanol, isodecanol, lauryl alcohol, myristyl alcohol, palmityl alcohol, butyl diglycol or a mixture thereof.

7. The process according to claim 2, wherein said tertiary amine is tri-(2-ethylhexyl)-amine.

8. The process according to claim 1, which further comprises partially separating the maleic anhydride by cooling to temperatures above the dew point of the accompanying water, prior to introducing the air stream of maleic anhydride and water vapor into the amine and hydrocarbon, amine and alcohol, or water of step (a).

9. The process according to claim 1, wherein said hydrocarbon capable of being air-oxidized to maleic anhydride is selected from the group of butane, butene, butadiene or benzene or a mixture thereof.

10. The process according to claim 1, wherein said hydrocarbon diluent entrainer for water is an aromatic hydrocarbon selected from the group consisting of xylene and diethylbenzene.

* * * * *